(12) United States Patent
Husson et al.

(10) Patent No.: US 6,548,515 B1
(45) Date of Patent: Apr. 15, 2003

(54) DIHYDROFURO[3,4-B]QUINOLIN-1-ONE COMPOUNDS

(75) Inventors: Henri-Philippe Husson, Chevreuse (FR); Sylviane Giorgi-Renault, Paris (FR); Christophe Tratrat, Paris (FR); Ghanem Atassi, Saint Cloud (FR); Alain Pierre, Les Alluets le Roi (FR); Pierre Renard, Le Chesnay (FR); Bruno Pfeiffer, Saint Leu la Foret (FR)

(73) Assignee: Les Laboratories Servier, Neuilly-sur-Seine (FR)

( * ) Notice: Subject to any disclaimer, the term of this patent is extended or adjusted under 35 U.S.C. 154(b) by 156 days.

(21) Appl. No.: 09/718,917

(22) Filed: Nov. 22, 2000

(30) Foreign Application Priority Data

Nov. 24, 1999 (FR) .............................................. 99.14771

(51) Int. Cl.$^7$ .................. A61K 31/4741; A61K 31/473; A61P 35/00; C07D 491/153; C07D 491/048; C07D 491/056

(52) U.S. Cl. ...................... 514/284; 514/280; 514/285; 514/287; 514/290; 514/291; 546/47; 546/61; 546/62; 546/65; 546/79; 546/89; 546/80; 546/102

(58) Field of Search ............................... 546/62, 65, 61, 546/89, 79, 102, 80, 47; 514/285, 287, 290, 291, 284, 280

(56) References Cited

U.S. PATENT DOCUMENTS 3,910,917 A * 10/1975 Meyer ..................... 260/279 R

OTHER PUBLICATIONS

Hitotsuyanagi Y et al. Tetrahedron Letters. 38(48), 8295–8296 (1997).*
Hitotsuyanagi Y et al. Bioorganic & Medicinal Chemistry Letters. 5(10), 1039–1042 (1995).*
Matsuo K et al. Chem. Express 8(6), 389–92 (1993).*
Sof'ina et al. National Cancer Institute Monograph 55. Experimental Evaluation of Antitumor Drugs in the USA and USSR and Clinical Correlations. NIH Publication No. 80–1933 (1980). pp. 76–78.*

* cited by examiner

Primary Examiner—Evelyn Mei Huang
(74) Attorney, Agent, or Firm—The Firm of Hueschen and Sage

(57) ABSTRACT

The invention relates to compound of formula (I):

wherein:
=== represents a single or double bond,
$R_0$ represents hydrogen or hydroxy or alkoxy,
$R_1$ and $R_2$, which are identical or different, each represents hydrogen or halogen or alkyl, alkoxy, hydroxy, polyhaloalkyl, nitro or optionally substituted amino or wherein m represents an integer such that $1 \leq m \leq 4$, or form together with the carbon atoms carrying them an aromatic or non-aromatic, mono- or bi-cyclic group having from 5 to 12 ring members and optionally containing 1 or 2 hetero atoms selected from O, S and N,
$R_3$ represents hydrogen or aryl, heteroaryl, cycloalkyl, optionally substituted alkyl or a group of formula $COR_7$ wherein $R_7$ represents aryl, optionally substituted alkyl, optionally substituted amino or $OR_{10}$ wherein $R_{10}$ represents aryl or optionally substituted alkyl,
X represents oxygen or sulphur or —$CH_2$— or —$CH_2$—$CH_2$—,
Ar represents aryl, heteroaryl or arylalkyl,
its optical isomers, its hydrates, solvates, and also its addition salts with a pharmaceutically acceptable acid.

Medicinal products containing the same are useful in the treatment of cancer.

22 Claims, No Drawings

DIHYDROFURO[3,4-B]QUINOLIN-1-ONE COMPOUNDS

FIELD OF THE INVENTION

The present invention relates to new dihydrofuro[3,4-b]quinolin-1-one compounds, and to the use thereof as anti-cancer agents.

BACKGROUND OF THE INVENTION

The requirements of anti-cancer therapeutics call for the constant development of new anti-tumour agents, with the aim of obtaining medicaments that are both more active and better tolerated.

The compounds of the invention are not only new but have very valuable anti-tumour properties.

DESCRIPTION OF THE PRIOR ART

Compounds of a similar structure have already been described in the literature, notably furo[3,4-b]quinolin-1-one compounds as anti-osteoporotics (patent EP 0 634 169).

On the other hand, a cytotoxic activity has never been described for those compounds.

DETAILED DESCRIPTION OF THE INVENTION

The present invention relates more especially to compounds of formula (I):

(I)

wherein:
=== represents a single or double bond,
$R_0$ represents a hydrogen atom, a hydroxy group or a linear or branched ($C_1$–$C_6$)alkoxy group,
$R_1$ and $R_2$, which are identical or different, each represents:
  a hydrogen atom,
  a halogen atom,
  a linear or branched ($C_1$–$C_6$)alkyl group,
  a linear or branched ($C_1$–$C_6$)alkoxy group,
  a hydroxy group,
  a linear or branched ($C_1$–$C_6$)polyhaloalkyl group,
  a nitro group,
  an amino group optionally substituted by one or two linear or branched ($C_1$–$C_6$)-alkyl groups,
  a group of formula $-N\underset{}{\triangleleft}{}_m$ wherein m represents an integer such that $1 \leq m \leq 4$, or form together with the carbon atoms carrying them an aromatic or non-aromatic, mono- or bi-cyclic group having from 5 to 12 ring members, optionally containing 1 or 2 hetero atoms selected from O, S and N, $R_3$ represents a hydrogen atom or a group of formula $R_4$ wherein $R_4$ represents:
  an aryl group,
  a heteroaryl group,
  a ($C_3$–$C_8$)cycloalkyl group,
  a linear or branched ($C_1$–$C_6$)alkyl group optionally substituted by an aryl group, by a heteroaryl group, by a hydroxy group, by a linear or branched ($C_1$–$C_6$) alkoxy group, or by a group of formula $NR_5R_6$ wherein $R_5$ and $R_6$, which are identical or different, each represents a linear or branched ($C_1$–$C_6$)alkyl group or a linear or branched ($C_1$–$C_6$)hydroxyalkyl group, or form together with the nitrogen atom carrying them a nitrogen heterocycle,
  or a group of formula $COR_7$, wherein $R_7$ represents one of the following groups:
    aryl,
    linear or branched ($C_1$–$C_6$)alkyl (optionally substituted by a group of formula $NR_8R_9$ wherein $R_8$ and $R_9$, which are identical or different, each represents a linear or branched ($C_1$–$C_6$)alkyl group or a linear or branched ($C_1$–$C_6$) hydroxyalkyl group, or form together with the nitrogen atom carrying them a nitrogen heterocycle),
    amino optionally substituted by one or more groups aryl, heteroaryl, or linear or branched ($C_1$–$C_6$) alkyl optionally substituted by a group of formula $NR_8R_9$ wherein $R_8$ and $R_9$, which are identical or different, each represents a linear or branched ($C_1$–$C_6$)alkyl group or a linear or branched ($C_1$–$C_6$)-hydroxyalkyl group, or form together with the nitrogen atom carrying them a nitrogen heterocycle,
    or $OR_{10}$ wherein $R_{10}$ represents a hydrogen atom or a group aryl, or linear or branched ($C_1$–$C_6$)alkyl optionally substituted by a group of formula $NR_8R_9$ wherein $R_8$ and $R_9$, which are identical or different, each represents a linear or branched ($C_1$–$C_6$)alkyl group or a linear or branched ($C_1$–$C_6$)hydroxyalkyl group, or form together with the nitrogen atom carrying them a nitrogen heterocycle, X represents an oxygen or sulphur atom or a —$CH_2$— or —$CH_2$—$CH_2$— group, Ar represents an aryl, heteroaryl or aryl-($C_1$–$C_6$)alkyl group in which alkyl is linear or branched, their optical isomers, addition salts thereof with a pharmaceutically acceptable acid, and hydrates and solvates thereof.

Among the pharmaceutically acceptable acids there may be mentioned, without implying any limitation, hydrochloric, hydrobromic, sulphuric, phosphoric, acetic, trifluoroacetic, lactic, pyruvic, malonic, succinic, glutaric, fumaric, tartaric, maleic, citric, ascorbic, oxalic, methanesulphonic, benzenesulphonic and camphoric acid.

An aryl group is to be understood as phenyl, biphenyl, naphthyl or tetrahydronaphthyl, each of those groups being optionally substituted by one or more identical or different atoms or groups selected from halogen atoms and the groups linear or branched ($C_1$–$C_6$)-alkyl, hydroxy, linear or branched ($C_1$–$C_6$)alkoxy, linear or branched ($C_1$–$C_6$) polyhaloalkyl, amino (optionally substituted by one or more linear or branched ($C_1$–$C_6$)alkyl groups), nitro, linear or branched ($C_1$–$C_6$)acyl and ($C_1$–$C_2$)alkylenedioxy.

A heteroaryl group is to be understood as an aromatic, mono- or bi-cyclic group having from 5 to 12 ring members and containing one, two or three hetero atoms selected from oxygen, nitrogen and sulphur, wherein the heteroaryl group may be optionally substituted by one or more identical or different atoms or groups selected from halogen atoms and the groups linear or branched ($C_1$–$C_6$)alkyl, hydroxy, linear or branched ($C_1$–$C_6$)alkoxy, linear or branched ($C_1$–$C_6$) polyhaloalkyl, and amino (optionally substituted by one or more linear or branched ($C_1$–$C_6$)alkyl groups). Among the heteroaryl groups there may be mentioned, without implying any limitation, the groups thienyl, pyridyl, furyl, pyrrolyl, imidazolyl, oxazolyl, isoxazolyl, thiazolyl, isothiazolyl, quinolyl, isoquinolyl and pyrimidinyl.

A nitrogen heterocycle is to be understood as a saturated monocyclic group having from 5 to 7 ring members and containing one, two or three hetero atoms, one of which is nitrogen while the additional hetero atom(s) optionally present is/are selected from oxygen, nitrogen and sulphur. Preferred nitrogen heterocycles are the groups pyrrolidinyl, piperidyl, morpholinyl and piperazinyl.

Among the aromatic or non-aromatic, mono- or bi-cyclic groups having from 5 to 12 ring members and optionally containing 1 or 2 hetero atoms selected from O, S and N there may be mentioned, without implying any limitation, the groups phenylene, naphthylene, cyclopentenylene and the groups of formulae $G_1$ to $G_5$:

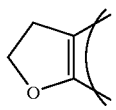
$G_1$

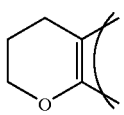
$G_2$

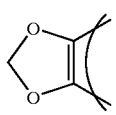
$G_3$

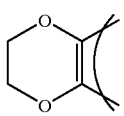
$G_4$

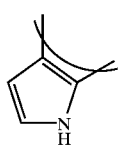
$G_5$

Preferred compounds of formula (I) are those wherein ═══ represents a double bond.

Preferred compounds of formula (I) are those wherein $R_0$ represents a hydrogen atom.

An advantageous embodiment of the invention relates to compounds of formula (I) wherein $R_1$ and $R_2$, which are identical or different, each represents a hydrogen atom, a halogen atom, a linear or branched ($C_1$–$C_6$)alkyl group, a linear or branched ($C_1$–$C_6$)alkoxy group, a hydroxy group, a linear or branched ($C_1$–$C_6$)polyhaloalkyl group, a nitro group, an amino group optionally substituted by one or two linear or branched ($C_1$–$C_6$)-alkyl groups, or a group of formula

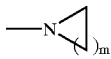

wherein m represents an integer such that $1 \leq m \leq 4$.

Another advantageous embodiment of the invention relates to compounds of formula (I) wherein $R_1$ and $R_2$ form together with the carbon atoms carrying them an aromatic or non-aromatic, mono- or bi-cyclic group having from 5 to 12 ring members and optionally containing 1 or 2 hetero atoms selected from O, S and N.

Among these are most preferred those wherein $R_1$ and $R_2$ together form, with the carbon atoms carrying them, a phenylene group or a group of formula $G_3$ or $G_4$ as defined hereinbefore.

Another advantageous embodiment of the invention relates to compounds of formula (I) wherein X represents an oxygen or sulphur atom.

Another advantageous embodiment of the invention relates to compounds of formula (I) wherein X represents a —$CH_2$— or —$CH_2$—$CH_2$— group.

Another advantageous embodiment of the invention relates to compounds of formula (I) wherein Ar represents an aryl group, more preferably an optionally substituted phenyl group.

Another advantageous embodiment of the invention relates to compounds of formula (I) wherein Ar represents a heteroaryl group.

Among the preferred compounds of the invention, there may be mentioned:

(±)-4-methyl-6,7-methylenedioxy-9-(3,4,5-trimethoxyphenyl)-4,9-dihydrofuro[3,4-b]quinolin-1(3H)-one, and also its optical isomers and its hydrates and solvates, (±)-6,7-methylenedioxy-9-(3,4,5-trimethoxyphenyl)-4,9-dihydrofuro[3,4-b]quinolin-1(3H)-one, its optical isomers, its hydrates, solvates, and also its addition salts with a pharmaceutically acceptable acid, (±)-6-methoxy-9-(3,4,5-trimethoxyphenyl)-4,9-dihydrofuro[3,4-b]quinolin-1(3H)-one, its optical isomers, its hydrates solvates, and also its addition salts with a pharmaceutically acceptable acid, (±)-7-(3,4,5-trimethoxyphenyl)-7,11-dihydrobenzo[h]furo[3,4-b]quinolin-8(10H)-one, its optical isomers, its hydrates, solvates, and also its addition salts with a pharmaceutically acceptable acid, (±)-6,7-methylenedioxy-9-(3,4,5-trimethoxyphenyl)-2,3,4,9-tetrahydrocyclopenta[b]quinolin-1-one, its optical isomers, its hydrates, solvates, and also its addition salts with a pharmaceutically acceptable acid, (±)-6,7-ethylenedioxy-9-(3,4,5-trimethoxyphenyl)-4,9-dihydrofuro[3,4-b]quinolin-1(3H)-one, its optical isomers, its hydrates, solvates, and also its addition salts with a pharmaceutically acceptable acid, and (±)-7-(3,4,5-trimethoxyphenyl)-7,9,10,11-tetrahydro-8H-benzo[h]cyclopenta[b]quinolin-8-one, its optical isomers, its hydrates, solvates, and also its addition salts with a pharmaceutically acceptable acid.

The invention relates also to a process for the preparation of the compounds of formula (I) which is characterised in that a compound of formula (II):

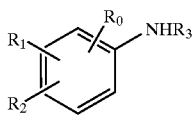

(II)

wherein $R_0$, $R_1$, $R_2$ and $R_3$ have the same meanings as for formula (I), is reacted with a compound of formula (III):

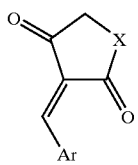

(III)

wherein X and Ar have the same meanings as for formula (I), to yield a compound of formula (Ia), a particular case of the compounds of formula (I):

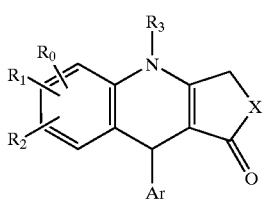

(Ia)

wherein $R_0$, $R_1$, $R_2$, $R_3$, X and Ar are as defined hereinbefore, which is then reduced, if desired, to a compound of formula (Ib), a particular case of the compounds of formula (I):

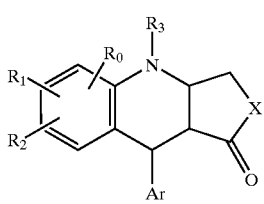

(Ib)

wherein $R_0$, $R_1$, $R_2$, $R_3$, X and Ar are as defined hereinbefore, which compounds of formulae (Ia) and (Ib), which constitute the totality of the compounds of formula (I), are purified, if necessary, according to a conventional purification technique, are separated, if desired, into their optical isomers according to a conventional separation technique, and are converted, if desired, into addition salts thereof with a pharmaceutically acceptable acid.

When $R_3$ does not represent a hydrogen atom, the compound of formula (II) can be obtained by reaction of a compound of formula (IV):

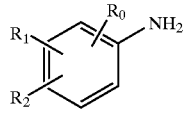

(IV)

wherein $R_0$, $R_1$ and $R_2$ are as defined hereinbefore, with a compound of formula (V):

(V)

wherein $R_4$ has the same meanings as for formula (I) and Y represents a leaving group, such as, for example, a halogen atom or a mesylate, tosylate or trifluoromethane-sulfonate group.

When $R_3$ represents a group of formula —$CH_2R'_3$ wherein $R'_3$ represents an aryl group, a heteroaryl group or a linear or branched ($C_1$–$C_5$)alkyl group optionally substituted by an aryl group, by a heteroaryl group, by a hydroxy group, by an optionally substituted, linear or branched ($C_1$–$C_6$)alkoxy group, or by a group of formula $NR_5R_6$ wherein $R_5$ and $R_6$, which are identical or different, each represents a linear or branched ($C_1$–$C_6$)-alkyl group or a linear or branched ($C_1$–$C_6$)hydroxyalkyl group, or form together with the nitrogen atom carrying them a nitrogen heterocycle, the compound of formula (II) can likewise be obtained by reaction, in the presence of a reducing agent, of a compound of formula (IV) with a compound of formula (VI):

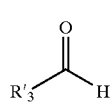

(VI)

wherein $R'_3$ is as defined hereinbefore.

When $R_3$ represents a group of formula —$COR'_7$ wherein $R'_7$ represents an aryl group, the compound of formula (II) can likewise be obtained by reaction of a compound of formula (VII):

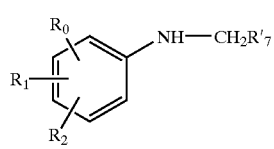

(VII)

wherein $R_0$, $R_1$, $R_2$ and $R'_7$ are as defined hereinbefore, with an oxidizing agent.

When $R_3$ represents a $CH_3$ group, the compound of formula (II) can likewise be obtained by reaction of a compound of formula (IV) with formic acid in the presence of a reducing agent.

The compound of formula (III) is obtained by reaction of a compound of formula (VIII):

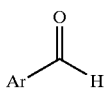

(VIII)

wherein Ar is as defined hereinbefore,
with a compound of formula (IX):

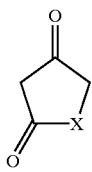

(IX)

wherein X is as defined hereinbefore,
in accordance with the procedure described in J. Org. Chem. 1978, 43, 1541.

The invention extends also to a second process for the preparation of the compounds of formula (I), which is characterised in that there are reacted, in the same pot, a compound of formula (II), a compound of formula (VII) and a compound of formula (VIII), to yield a compound of formula (Ia), which is then reduced, if desired, to a compound of formula (Ib), which compounds of formulae (Ia) and (Ib), which constitute the totality of the compounds of formula (I), are purified, if necessary, according to a conventional purification technique, are separated, if desired, into their optical isomers according to a conventional separation technique, and are converted, if desired, into addition salts thereof with a pharmaceutically acceptable acid.

The compounds of the present invention are not only new but exhibit valuable pharmacological properties. They exhibit cytotoxic properties, rendering them useful in the treatment of cancers.

The invention extends also to pharmaceutical compositions comprising as active ingredient at least one compound of formula (I) with one or more appropriate, inert, non-toxic excipients. Among the pharmaceutical compositions according to the invention there may be mentioned more especially those which are suitable for oral, parenteral (intravenous, intramuscular or subcutaneous) or nasal administration, tablets or dragees, sublingual tablets, gelatin capsules, lozenges, suppositories, creams, ointments, dermal gels, injectable preparations, drinkable suspensions, etc.

The useful dosage can be adapted in accordance with the nature and severity of the disorder, the administration route, the age and weight of the patient, and possibly associated treatments. The posology varies from 0.5 mg to 2 g per 24 hours taken in one or more administrations.

The following Examples illustrate the invention but do not limit it in any way.

The starting materials employed are known products or products prepared in accordance with known preparation procedures.

Preparations A to S result in synthesis intermediates for use in the preparation of the compounds of the invention.

The structures of the compounds described in the Examples were determined in accordance with customary spectrometric techniques (infra-red, NMR, mass spectrometry).

Preparation A: 3-(3,4,5-Trimethoxybenzylidene)-2, 4-(3H,5H)-furandione

The expected product is obtained in accordance with the procedure described in J. Org. Chem. 1978, 43, 1541, starting from 3,4,5-trimethoxybenzaldehyde and tetronic acid.

Preparation B: 3-(4-Hydroxy-3,5-dimethoxybenzylidene)-2,4-(3H,5H)-furandione

The expected product is obtained in accordance with the procedure described in J. Org. Chem. 1978, 43, 1541, starting from 4-hydroxy-3,5-dimethoxybenzaldehyde and tetronic acid.

Preparation C: 3-(3-Pyridylmethylene)-2,4-(3H,5H)-furandione

The expected product is obtained in accordance with the procedure described in J. Org. Chem. 1978, 43, 1541, starting from nicotinaldehyde and tetronic acid.

Preparation D: 3-(3-Methoxy4,5-methylenedioxybenzylidene)-2,4-(3H,5H)-furandione The expected product is obtained in accordance with the procedure described in J. Org. Chem. 1978, 43, 1541, starting from 3-methoxy-4,5-methylenedioxybenzaldehyde and tetronic acid.

Preparation E: 3-(2,3,4-Trimethoxybenzylidene)-2, 4-(3H,5H)-furandione

The expected product is obtained in accordance with the procedure described in J. Org. Chem. 1978, 43, 1541, starting from 2,3,4-trimethoxybenzaldehyde and tetronic acid.

Preparation F: 3-(3,4-Dimethoxybenzylidene)-2,4-(3H,5H)-furandione

The expected product is obtained in accordance with the procedure described in J. Org. Chem. 1978, 43, 1541, starting from 3,4-dimethoxybenzaldehyde and tetronic acid.

Preparation G: 3-(3-Hydroxy-4-metboxybenzylidene)-2,4-(3H,5H)-furandione

The expected product is obtained in accordance with the procedure described in J. Org. Chem. 1978, 43, 1541, starting from 3-hydroxy-4-methoxybenzaldehyde and tetronic acid.

Preparation H: 3-(4-Methoxybenzylidene)-2,4-(3H, 5H)-furandione

The expected product is obtained in accordance with the procedure described in J. Org. Chem. 1978, 43, 1541, starting from 4-methoxybenzaldehyde and tetronic acid.

Preparation I: 3-(3-Methoxybenzylidene)-2,4-(3H, 5H)-furandione

The expected product is obtained in accordance with the procedure described in J. Org. Chem. 1978, 43, 1541, starting from 3-methoxybenzaldehyde and tetronic acid.

Preparation J: 3-Benzylidene-2,4-(3H,5H)-furandione

The expected product is obtained in accordance with the procedure described in J. Org. Chem. 1978, 43, 1541, starting from benzaldehyde and tetronic acid.

Preparation K: 3-(2-Furylmethylene)-2,4-(3H,5H)-furandione

The expected product is obtained in accordance with the procedure described in J. Org. Chem. 1978. 43, 1541, starting from 2-furaldehyde and tetronic acid.

Preparation L: 3-(3,4,5-Trimethoxybenzylidene)-1,
3-cyclopentanedione

The expected product is obtained in accordance with the procedure described in J. Org. Chem. 1978, 43, 1541, starting from 3,4,5-trimethoxybenzaldehyde and 1,3-cyclopentane-dione.

Preparation M: 3-(4,5-Methylenedioxybenzylidene)-
2,4-(3H,5H)-furandione

The expected product is obtained in accordance with the procedure described in J. Org. Chem. 1978, 43, 1541, starting from 4,5-methylenedioxybenzaldehyde and tetronic acid.

Preparation N: 3-(4-Chlorobenzylidene)-2,4-(3H,
5H)-furandione

The expected product is obtained in accordance with the procedure described in J. Org. Chem. 1978, 43, 1541, starting from 4-chlorobenzaldehyde and tetronic acid.

Preparation O: 3-(4-Nitrobenzylidene)-2,4-(3H,5H)-
furandione

The expected product is obtained in accordance with the procedure described in J. Org. Chem. 1978, 43, 1541, starting from 4-nitrobenzaldehyde and tetronic acid.

Preparation P: 3-(3-Nitrobenzylidene)-2,4-(3H,5H)-
furandione

The expected product is obtained in accordance with the procedure described in J. Org. Chem. 1978, 43, 1541, starting from 3-nitrobenzaldehyde and tetronic acid.

Preparation Q: 3-(4-Dimethylaminobenzylidene)-2,
4-(3H,5H)-furandione

The expected product is obtained in accordance with the procedure described in J. Org. Chem. 1978, 43, 1541, starting from 4-dimethylaminobenzaldehyde and tetronic acid.

Preparation R: 3-(4-Pyridylmethylene)-2,4-(3H,5H)-
furandione

The expected product is obtained in accordance with the procedure described in J. Org. Chem. 1978, 43, 1541, starting from isonicotinaldehyde and tetronic acid.

Preparation S: 3-(2-Pyridylmethylene)-2,4-(3H,5H)-
furandione

The expected product is obtained in accordance with the procedure described in J. Org. Chem. 1978, 43, 1541, starting from 2-pyridinecarboxaldehyde and tetronic acid.

EXAMPLE 1

($\pm$)-4-Methyl-6,7-methylenedioxy-9-(3,4,5-
trimethoxyphenyl)-4,9-dihydrofuro[3,4-b]quinolin-1
(3H)-one Step A: N-methyl-3,4-methylenedioxyaniline A solution of 3,4-methylenedioxyaniline (10 mmol) in formic acid (36 ml) is heated at reflux for 1 hour. After the removal of excess formic acid, the residue obtained is diluted with water and then extracted with dichloromethane. The combined organic phases are evaporated. The residue obtained is dissolved in ether, then lithium aluminium hydride (42 mmol) is added at 10° C., in small portions. After stirring the mixture at ambient temperature for 3 hours, water and 10% sodium hydroxide solution are added and the mixture is then filtered over Celite. The filtrate is dried and evaporated and the residue obtained is purified by chromatography on silica, using dichloromethane as eluant, to yield the expected product in the form of an oil.

Step B: ($\pm$)-4-Methyl-6,7-methylenedioxy-9-(3,4,5-
trimethoxyphenyl)-4,9-dihydrofuro[3,4-b]quinolin-1
(3H)-one 10 mmol of the compound described in Preparation A are added to the compound obtained in the above Step (10 mmol) suspended in ethanol, then the mixture is heated at reflux for 30 minutes. After returning to ambient temperature, the precipitate obtained is filtered and washed and then recrystallised to yield the expected product.

Melting point: 226° C.

| Elemental microanalysis: | | | |
|---|---|---|---|
| | % C | % H | % N |
| Calculated: | 64.23 | 5.14 | 3.40 |
| Found: | 64.11 | 5.09 | 3.26 |

EXAMPLE 2

($\pm$)-4-Methyl-6,7-methylenedioxy-9-(3,4,5-
trimethoxyphenyl)-3a,4,9,9a-tetrahydrofuro[3,4-b]
quinolin-1(3H)-one A suspension of the compound described in Example 1 (10 mmol) in ethanol is placed under hydrogen pressure (50 psi) at ambient temperature in the pressence of palladium-on-carbon. After removal of the catalyst by filtration, the solvent is evaporated off and the residue obtained is purified by chromatography on silica using dichloromethane as eluant.

EXAMPLE 3

($\pm$)-6,7-Methylenedioxy-4-(4-nitrobenzyl)-9-(3,4,5-
trimethoxyphenyl)-4,9-dihydrofuro[3,4-b]quinolin-1
(3H)-one Step A: N-(4-Nitrobenzyl)-3,4-
methylenedioxyaniline A solution of 3,4-methylenedioxyaniline (10 mmol) and 4-nitrobenzaldehyde (10 mmol) in methanol is stirred at ambient temperature for 18 hours. The precipitate obtained is filtered off and washed and then dissolved in tetrahydrofuran. After the addition of acetic acid and sodium borohydride (25 mmol), the reaction mixture is stirred at ambient temperature for 1 hour, then the solvent is evaporated off and the crude residue is purified by chromatography on silica using dichloromethane as eluant.

Melting point: 114° C.

Step B: ($\pm$)-6,7-Methylenedioxy-4-(4-nitrobenzyl)-
9-(3,4,5-trimethoxyphenyl)-4,9-dihydrofuro[3,4-b]
quinolin-1(3H)-one The expected product is obtained in accordance with the procedure described in Step B of Example 1, starting from the compound obtained in the above Step and the compound described in Preparation A.

Melting point: 240° C.

Elemental microanalysis: (hemihydrate)

|  | % C | % H | % N |
|---|---|---|---|
| Calculated: | 62.11 | 4.80 | 5.17 |
| Found: | 62.43 | 4.49 | 5.13 |

EXAMPLE 4

(±)-4-(4-Chlorobenzyl)-6,7-methylenedioxy-9-(3,4,5-trimethoxyphenyl)-4,9-dihydrofuro[3,4-b]quinolin-1(3H)-one The expected product is obtained in accordance with the procedure described in Example 3, starting from 3,4-methylenedioxyaniline, 4-chlorobenzaldehyde and the compound described in Preparation A.

Melting point: >260° C.

Elemental microanalysis: (hemihydrate)

|  | % C | % H | % N |
|---|---|---|---|
| Calculated: | 63.34 | 4.74 | 2.64 |
| Found: | 63.51 | 4.73 | 2.59 |

EXAMPLE 5

(±)-4-(3-Hydroxybenzyl)-6,7-methylenedioxy-9-(3,4,5-trimethoxyphenyl)-4,9-dihydrofuro[3,4-b]quinolin-1(3H)-one The expected product is obtained in accordance with the procedure described in Example 3, starting from 3,4-methylenedioxyaniline, 3-hydroxybenzaldehyde and the compound described in Preparation A.

Melting point: 245° C.

Elemental microanalysis: (hydrate)

|  | % C | % H | % N |
|---|---|---|---|
| Calculated: | 64.49 | 5.22 | 2.68 |
| Found: | 64.71 | 4.99 | 2.58 |

EXAMPLE 6

(±)-6,7-Methylenedioxy-4-(3,4-methylenedioxybenzyl)-9-(3,4,5-trimethoxyphenyl)-4,9-dihydrofuro[3,4-b]quinolin-1(3H)-one The expected product is obtained in accordance with the procedure described in Example 3, starting from 3,4-methylenedioxyaniline, 3,4-methylenedioxybenzaldehyde and the compound described in Preparation A.

Melting point: >260° C.

Elemental microanalysis: (hydrate)

|  | % C | % H | % N |
|---|---|---|---|
| Calculated: | 63.38 | 4.95 | 2.55 |
| Found: | 63.72 | 4.73 | 2.51 |

EXAMPLE 7

(±)-6,7-Methylenedioxy-4-(3,4,5-trimethoxybenzyl)-9-(3,4,5-trimethoxyphenyl)-4,9-dihydrofuro[3,4-b]quinolin-1(3I)-one The expected product is obtained in accordance with the procedure described in Example 3, starting from 3,4-methylenedioxyaniline, 3,4,5-trimethoxybenzaldehyde and the compound described in Preparation A.

Melting point: 190° C.

Elemental microanalysis: (hemihydrate)

|  | % C | % H | % N |
|---|---|---|---|
| Calculated: | 63.47 | 5.50 | 2.39 |
| Found: | 63.58 | 5.59 | 2.65 |

EXAMPLE 8

(±)-4-(3,5-Dimethoxy-4-hydroxybenzyl)-6,7-methylenedioxy-9-(3,4,5-trimethoxyphenyl)-4,9-dihydrofuro[3,4-b]quinolin-1(3H)-one The expected product is obtained in accordance with the procedure described in Example 3, starting from 3,4-methylenedioxyaniline, 3,5-dimethoxy4-hydroxybenzaldehyde and the compound described in Preparation A.

Melting point: 242° C.

Elemental microanalysis:

|  | % C | % H | % N |
|---|---|---|---|
| Calculated: | 63.94 | 5.19 | 2.49 |
| Found: | 63.72 | 5.21 | 2.46 |

EXAMPLE 9

(±)-4-(2-Hydroxyethyl)-6,7-methylenedioxy-9-(3,4,5-trimethoxyphenyl)-4,9-dihydrofuro[3,4-b]quinolin-1 (3H)-one Step A: N-(3,4-Methylenedioxyphenyl)-2-aminoethanol 27 mmol of sodium acetate and 15 mmol of 2-bromoethanol are added to 10 mmol of 3,4-methylenedioxyaniline dissolved in ethanol. After 24 hours of heating at reflux, the reaction mixture is brought to ambient temperature, water is added, and then the aqueous phase is extracted with dichloromethane. The organic phases are combined, the solvent is evaporated off and the crude residue is purified by chromatography on silica, using a 10:90 dichloromethane/ethyl acetate mixture as eluant, to yield the expected product in the form of an oil.

Step B: (±)-4-(2-Hydroxyethyl)-6,7-methylenedioxy-9-(3,4,5-trimethoxyphenyl)-4,9-dihydrofuro[3,4-b]quinolin-1(3H)-one The expected product is obtained in accordance with the procedure described in Step B of Example 1, starting from the compound described in the above Step and the compound described in Preparation A.

Melting point: >260° C.

Elemental microanalysis: (hemihydrate)

|  | % C | % H | % N |
|---|---|---|---|
| Calculated: | 61.33 | 5.37 | 3.11 |
| Found: | 61.54 | 5.28 | 2.94 |

EXAMPLE 10

(±)-6,7-Methylenedioxy-9-(3,4,5-trimethoxyphenyl)-4,9-dihydrofuro[3,4-b]quinolin-1(3H)-one The expected product is obtained in accordance with the procedure described in Step B of Example 1, starting from 3,4-methylenedioxyaniline and the compound described in Preparation A.

Melting point: >260° C.

Elemental microanalysis:

|  | % C | % H | % N |
|---|---|---|---|
| Calculated | 63.47 | 4.82 | 3.52 |
| Found: | 63.32 | 4.86 | 3.45 |

EXAMPLE 11

(±)-6,7-Methylenedioxy-4-propyl-9-(3,4,5-trimethoxyphenyl)-4,9-dihydrofuro[3,4-b]quinolin-1(3H)-one The expected product is obtained in accordance with the procedure described in Example 9, starting from 3,4-methylenedioxyaniline, propyl bromide and the compound described in Preparation A.

Melting point: 230° C.

EXAMPLE 12

(±)-4-(N,N-Dimethylaminopropyl)-6,7-methylenedioxy-9-(3,4,5-trimethoxyphenyl)-4,9-dihydrofuro[3,4-b]quinolin-1(3H)-one The expected product is obtained in accordance with the procedure described in Example 9, starting from 3,4-methylenedioxyaniline, 3-chloro-1-dimethylaminopropane and the compound described in Preparation A.

Melting point: 182° C.

EXAMPLE 13

(±)-4,9-Bis-(3,4,5-trimethoxyphenyl)-6,7-methylenedioxy-4,9-dihydrofuro[3,4-b]quinolin-1(3H)-one Step A: N-(3,4-Methylenedioxyphenyl)-3,4,5-trimethoxyaniline 10 mmol of 3,4,5-trimethoxyiodobenzene, 0.4 mmol of palladium acetate, 0.4 mmol of 2,2'-bis(diphenylphosphino)-1,1'-bi naphthyl and 14 mmol of potassium tert-butanolate are added to 10 mmol of 3,4-methylenedioxyaniline dissolved in toluene. After heating for 15 minutes at 100° C., the reaction mixture is brought to ambient temperature, and then dichloromethane and water are added. The organic phase is subsequently separated off and distilled under reduced pressure. The residue is purified by chromatography on silica, using dichloromethane as eluant, to yield the expected product in the form of an oil.

IR (film): 3361, 2934, 1602, 1503, 1488, 1232, 1204, 1128, 1037, 930 and 813 cm$^{-1}$ Step B: (±)-4,9-Bis-(3,4,5-trimethoxyphenyl)-6,7-methylenedioxy-4,9-dihydrofuro[3,4-b]quinolin-1(3H)-one The expected product is obtained in accordance with the procedure described in Step B of Example 1, starting from the compound obtained in the above Step and the compound described in Preparation A.

Melting point: >260° C.

Elemental microanalysis: (hemihydrate)

|  | % C | % H | % N |
|---|---|---|---|
| Calculated: | 62.93 | 5.28 | 2.44 |
| Found: | 62.73 | 5.11 | 2.21 |

EXAMPLE 14

(±)-6,7-Dimethoxy-9-(3,4,5-trimethoxyphenyl)-4,9-dihydrofuro-[3,4-b]quinolin-1(3H)-one The expected product is obtained in accordance with the procedure described in Step B of Example 1, starting from 3,4-dimethoxyaniline and the compound described in Preparation A.

Melting point: 218° C.

EXAMPLE 15

(±)-9-(3,5-Dimethoxy-4-hydroxyphenyl)-4-methyl-6,7-methylenedioxy-4,9-dihydrofuro[3,4-b]quinolin-1(3H)-one The expected product is obtained in accordance with the procedure described in Step B of Example 1, starting from the compound described in Step A of Example 1 and the compound described in Preparation B.

Melting point: 250° C.

Elemental microanalysis: (hydrate)

|  | % C | % H | % N |
|---|---|---|---|
| Calculated: | 60.72 | 4.85 | 3.37 |
| Found: | 60.78 | 4.99 | 3.14 |

EXAMPLE 16

(±)-9-(3,5-Dimethoxy-4-hydroxyphenyl)-6,7-methylenedioxy-4-(4-nitrobenzyl)-4,9-dihydrofuro[3,4-b]quinolin-1(3H)-one The expected product is obtained in accordance with the procedure described in Step B of Example 1, starting from the compound described in Step A of Example 3 and the compound described in Preparation B.

Melting point: 193° C.

Elemental microanalysis: (hemihydrate)

|  | % C | % H | % N |
|---|---|---|---|
| Calculated: | 61.48 | 4.30 | 5.31 |
| Found: | 61.61 | 4.36 | 5.11 |

EXAMPLE 17

(±)-4-(4-Chlorobenzyl)-9-(3,5-dimethoxy-4-hydroxyphenyl)-6,7-methylenedioxy-4,9-dihydrofuro[3,4-b]quinolin-1(3H)-one The expected product is obtained in accordance with the procedure described in Example 3, starting from 3,4-methylenedioxyaniline, 4-chlorobenzaldehyde and the compound described in Preparation B.

Melting point: 252° C.

EXAMPLE 18

(±)-9-(3,5-Dimethoxy-4-hydroxyphenyl)-4-(3-hydroxybenzyl)-6,7-methylenedioxy-4,9-dihydrofuro[3,4-b]quinolin-1(3H)-one The expected product is obtained in accordance with the procedure described in Example 3, starting from 3,4-methylenedioxyaniline, 3-hydroxybenzaldehyde and the compound described in Preparation B.

Melting point: 220° C.

Elemental microanalysis: ($C_{27}H_{23}NO_8$.1.5 $H_2O$)

|  | % C | % H | % N |
|---|---|---|---|
| Calculated: | 62.79 | 5.07 | 2.71 |
| Found: | 62.44 | 4.89 | 2.75 |

EXAMPLE 19

(±)-9-(3,5-Dimethoxy-4-hydroxyphenyl)-6,7-methylenedioxy-4-(3,4-methylenedioxybenzyl)-4,9-dihydrofuro[3,4-b]quinolin-1(3H)-one The expected product is obtained in accordance with the procedure described in Example 3, starting from 3,4-methylenedioxyaniline, 3,4-methylenedioxybenzaldehyde and the compound described in Preparation B.

Melting point: >260° C.

Elemental microanalysis: (hemihydrate)

|  | % C | % H | % N |
|---|---|---|---|
| Calculated: | 63.88 | 4.59 | 2.66 |
| Found: | 63.89 | 4.51 | 2.69 |

EXAMPLE 20

(±)-9-(3,5-Dimethoxy-4-hydroxyphenyl)-6,7-methylenedioxy-4-(3,4,5-trimethoxybenzyl)-4,9-dihydrofuro[3,4-b]quinolin-1(3H)-one The expected product is obtained in accordance with the procedure described in Example 3, starting from 3,4-methylenedioxyaniline, 3,4,5-trimethoxybenzaldehyde and the compound described in Preparation B.

Melting point: 165° C.

Elemental microanalysis: ($C_{30}H_{29}NO_{10}$.2.5 $H_2O$)

|  | % C | % H | % N |
|---|---|---|---|
| Calculated: | 59.21 | 5.63 | 2.30 |
| Found: | 59.22 | 5.51 | 2.34 |

EXAMPLE 21

(±)-4-(3,5-Dimethoxy-4-hydroxybenzyl)-9-(3,5-dimethoxy-4-hydroxyphenyl)-6,7-methylenedioxy-4,9-dihydrofuro[3,4-b]quinolin-1(3H)-one The expected product is obtained in accordance with the procedure described in Example 3, starting from 3,4-methylenedioxyaniline, 3,5-dimethoxy-4-hydroxybenzaldehyde and the compound described in Preparation B.

Melting point: 235° C.

Elemental microanalysis: (hemihydrate)

|  | % C | % H | % N |
|---|---|---|---|
| Calculated: | 62.36 | 5.05 | 2.51 |
| Found: | 62.16 | 4.96 | 2.34 |

EXAMPLE 22

(±)-9-3,5-Dimethoxy-4-hydroxyphenyl)-4-(2-hydroxyethyl)-6,7-methylenedioxy-4,9-dihydrofuro[3,4-b]quinolin-1(3H)-one The expected product is obtained in accordance with the procedure described in Step B of Example 1, starting from the compound described in Step A of Example 9 and the compound described in Preparation B.

Melting point: >260° C.

Elemental microanalysis: (hemihydrate)

|  | % C | % H | % N |
|---|---|---|---|
| Calculated: | 60.55 | 5.08 | 3.21 |
| Found: | 60.84 | 5.05 | 3.11 |

EXAMPLE 23

(±)-9-(3,5-Dimethoxy-4-hydroxyphenyl)-6-methyl-4,9-dihydrofuro[3,4-b]quinolin-1(3H)-one The expected product is obtained in accordance with the procedure described in Step B of Example 1, starting from m-toluidine and the compound described in Preparation B.

EXAMPLE 24

(±)-6,7-Methylenedioxy-9-(3-pyridyl)-4,9-dihydrofuro[3,4-b]quinolin-1(3H)-one

The expected product is obtained in accordance with the procedure described in Step B of Example 1, starting from 3,4-methylenedioxyaniline and the compound described in Preparation C.

Melting point: >260° C.

| Elemental microanalysis: (hemihydrate) | | | |
|---|---|---|---|
| | % C | % H | % N |
| Calculated: | 64.35 | 4.13 | 8.83 |
| Found: | 64.14 | 4.15 | 8.61 |

EXAMPLE 25

(±)-6,7-Ethylenedioxy-9-(3-methoxy-4,5-methylenedioxyphenyl)-4-[(2-thienyl)methyl]-4,9-dihydrofuro[3,4-b]quinolin-1(3H)-one The expected product is obtained in accordance with the procedure described in Example 3, starting from 3,4-ethylenedioxyaniline, thiophene-2-carboxaldehyde and the compound described in Preparation D.

EXAMPLE 26

(±)-4-(Dimethylaminoethylcarbonyl)-9-(3-methoxy-4,5-methylenedioxyphenyl)-6,7-methylenedioxy-4,9-dihydrofuro[3,4-b]quinolin-1(3H)-one The expected product is obtained in accordance with the procedure described in Example 9, starting from 3,4-methylenedioxyaniline, 3-(dimethylamino)propionyl chloride and the compound described in Preparation D.

EXAMPLE 27

(±)-6-Methoxy-9-(3,4,5-trimethoxyphenyl)-4,9-dihydrofuro[3,4-b]quinolin-1(3H)-one The expected product is obtained in accordance with the procedure described in Step B of Example 1, starting from 3-methoxyaniline and the compound described in Preparation A.

Melting point: >260° C.

| Elemental microanalysis: | | | |
|---|---|---|---|
| | % C | % H | % N |
| Calculated: | 65.79 | 5.52 | 3.65 |
| Found: | 65.80 | 5.60 | 3.50 |

EXAMPLE 28

(±)-6,7,8-Trimethoxy-9-(3,4,5-trimethoxyphenyl)-4,9-dihydrofuro[3,4-b]quinolin-1(3H)-one The expected product is obtained in accordance with the procedure described in Step B of Example 1, starting from 3,4,5-trimethoxyaniline and the compound described in Preparation A.

| Elemental microanalysis: | | | |
|---|---|---|---|
| | % C | % H | % N |
| Calculated: | 61.05 | 5.79 | 3.09 |
| Found: | 61.19 | 6.02 | 3.00 |

EXAMPLE 29

(±)-6-Hydroxy-9-(3,4,5-trimethoxyphenyl)-4,9-dihydrofuro[3,4-b]quinolin-1(3H)-one The expected product is obtained in accordance with the procedure described in Step B of Example 1, starting from 3-aminophenol and the compound described in Preparation A.

Melting point: >260° C.

| Elemental microanalysis: (0.25 $H_2O$) | | | |
|---|---|---|---|
| | % C | % H | % N |
| Calculated: | 64.25 | 5.26 | 3.74 |
| Found: | 64.41 | 5.24 | 3.62 |

EXAMPLE 30

(±)-6,8-Dimethoxy-9-(3,4,5-trimethoxyphenyl)-4,9-dihydrofuro[3,4-b]quinolin-1(3H)-one The expected product is obtained in accordance with the procedure described in Step B of Example 1, starting from 3,5-dimethoxyaniline and the compound described in Preparation A.

Melting point: >260° C.

| Elemental microanalysis: | | | |
|---|---|---|---|
| | % C | % H | % N |
| Calculated: | 63.91 | 5.61 | 3.39 |
| Found: | 63.85 | 5.77 | 3.24 |

EXAMPLE 31

(±)-6,7-Methylenedioxy-9-(2,3,4-trimethoxyphenyl)-4,9-dihydrofuro[3,4-b]quinolin-1(3H)-one The expected product is obtained in accordance with the procedure described in Step B of Example 1, starting from 3,4-methylenedioxyaniline and the compound described in Preparation E.

Melting point: >260° C.

| Elemental microanalysis: | | | |
|---|---|---|---|
| | % C | % H | % N |
| Calculated: | 63.47 | 4.82 | 3.52 |
| Found: | 63.57 | 4.91 | 3.34 |

EXAMPLE 32

(±)-9-(3,4-Dimethoxyphenyl)-6,7-methylenedioxy-4, 9-dihydrofuro[3,4-b]quinolin-1(3H)-one The expected product is obtained in accordance with the procedure described in Step B of Example 1, starting from 3,4-methylenedioxyaniline and the compound described in Preparation F.

Melting point: >260° C.

| Elemental microanalysis: | | | |
|---|---|---|---|
| | % C | % H | % N |
| Calculated: | 65.39 | 4.66 | 3.81 |
| Found: | 64.87 | 4.73 | 3.52 |

EXAMPLE 33

(±)-9-(3-Hydroxy-4-methoxyphenyl)-6,7-methylenedioxy-4,9-dihydrofuro[3,4-b]quinolin-1(3H)-one The expected product is obtained in accordance with the procedure described in Step B of Example 1, starting from 3,4-methylenedioxyaniline and the compound described in Preparation G.

Melting point: >260° C.

| Elemental microanalysis: | | | |
|---|---|---|---|
| | % C | % H | % N |
| Calculated: | 64.59 | 4.28 | 3.96 |
| Found: | 64.75 | 4.25 | 3.76 |

EXAMPLE 34

(±)-9-(4-Methoxyphenyl)-6,7-methylenedioxy-4,9-dihydrofuro[3,4-b]quinolin-1(3H)-one The expected product is obtained in accordance with the procedure described in Step B of Example 1, starting from 3,4-methylenedioxyaniline and the compound described in Preparation H.

Melting point: >260° C.

| Elemental microanalysis: | | | |
|---|---|---|---|
| | % C | % H | % N |
| Calculated: | 67.65 | 4.48 | 4.15 |
| Found: | 67.98 | 4.43 | 3.95 |

EXAMPLE 35

(±)-9-(3-Methoxyphenyl)-6,7-methylenedioxy-4,9-dihydrofuro[3,4-b]quinolin-1(3H)-one The expected product is obtained in accordance with the procedure described in Step B of Example 1, starting from 3,4-methylenedioxyaniline and the compound described in Preparation I.

Melting point: >260° C.

| Elemental microanalysis: | | | |
|---|---|---|---|
| | % C | % H | % N |
| Calculated: | 67.65 | 4.48 | 4.15 |
| Found: | 67.48 | 4.49 | 3.97 |

EXAMPLE 36

(±)-6,7-Methylenedioxy-9-phenyl-4,9-dihydrofuro[3,4-b]quinolin-1(3H)-one

The expected product is obtained in accordance with the procedure described in Step B of Example 1, starting from 3,4-methylenedioxyaniline and the compound described in Preparation J.

Melting point: >260° C.

| Elemental microanalysis: | | | |
|---|---|---|---|
| | % C | % H | % N |
| Calculated: | 70.35 | 4.26 | 4.56 |
| Found: | 70.28 | 4.18 | 4.38 |

EXAMPLE 37

(±)-9-(2-Furyl)-6,7-methylenedioxy-4,9-dihydrofuro[3,4-b]quinolin-1(3H)-one

The expected product is obtained in accordance with the procedure described in Step B of Example 1, starting from 3,4-methylenedioxyaniline and the compound described in Preparation K.

Melting point: >260° C.

| Elemental microanalysis: | | | |
|---|---|---|---|
| | % C | % H | % N |
| Calculated: | 64.65 | 3.73 | 4.71 |
| Found: | 62.25 | 3.87 | 4.31 |

EXAMPLE 38

(±)-7-(3,4,5-Trimethoxyphenyl)-7,11-dihydrobenzo[h]furo[3,4-b]quinolin-8(10H)-one The expected product is obtained in accordance with the procedure described in Step B of Example 1, starting from 1-naphthylamine and the compound described in Preparation A.

Melting point: >260° C.

| Elemental microanalysis: (hemihydrate) | | | |
|---|---|---|---|
| | % C | % H | % N |
| Calculated: | 69.89 | 5.34 | 3.39 |
| Found: | 70.28 | 5.40 | 3.31 |

EXAMPLE 39

(±)-11-(3,4,5-Trimethoxyphenyl)-7,11-dihydrobenzo[f]furo[3,4-b]quinolin-10(8H)-one The expected product is obtained in accordance with the procedure described in Step B of Example 1, starting from 2-naphthylamine and the compound described in Preparation A.

Melting point: >260° C.

| Elemental microanalysis: | | | |
|---|---|---|---|
| | % C | % H | % N |
| Calculated: | 71.45 | 5.25 | 3.47 |
| Found: | 69.90 | 5.44 | 3.44 |

EXAMPLE 40

(±)-6,7-Methylenedioxy-9-(3,4,5-trimethoxyphenyl)-2,3,4,9-tetrahydrocyclopenta[b]quinolin-1-one The expected product is obtained in accordance with the procedure described in Step B of Example 1. starting from 3,4-methylenedioxyaniline and the compound described in Preparation L.

Melting point: >260° C.

| Elemental microanalysis: (0.25 $H_2O$) | | | |
|---|---|---|---|
| | % C | % H | % N |
| Calculated: | 66.07 | 5.42 | 3.50 |
| Found: | 66.09 | 5.34 | 3.36 |

EXAMPLE 41

(±)-6,7-Methylenedioxy-9-(3,4-methylenedioxyphenyl)-4,9-dihydrofuro[3,4-b]quinolin-1(3H)-one The expected product is obtained in accordance with the procedure described in Step B of Example 1, starting from 3,4-methylenedioxyaniline and the compound described in Preparation M.

Melting point: >260° C.

| Elemental microanalysis: | | | |
|---|---|---|---|
| | % C | % H | % N |
| Calculated: | 64.96 | 3.73 | 3.99 |
| Found: | 65.12 | 4.19 | 3.75 |

EXAMPLE 42

(±)-10-(3,4,5-Trimethoxyphenyl)-1,6,7,10-tetrahydro-9H-furo[3,4-b]pyrrolo[2,3-f]quinolin-9-one The expected product is obtained in accordance with the procedure described in Step B of Example 1, starting from 1H-indol-6-amine and the compound described in Preparation A.

Melting point: >260° C.

| Elemental microanalysis: (0.75 $H_2O$) | | | |
|---|---|---|---|
| | % C | % H | % N |
| Calculated: | 65.10 | 5.34 | 6.90 |
| Found: | 65.25 | 5.23 | 6.50 |

EXAMPLE 43

(±)-4-Benzyl-6,7-methylenedioxy-9-(3,4,5-trimethoxyphenyl)-4,9-dihydrofuro[3,4-b]quinolin-1(3H)-one The expected product is obtained in accordance with the procedure described in Example 3, starting from 3,4-methylenedioxyaniline, benzaldehyde and the compound described in Preparation A.

Melting point: 236° C.

EXAMPLE 44

(±)-9-(4-Chlorophenyl)-6,7-methylenedioxy-4,9-dihydrofuro[3,4-b]quinolin-1(3H)-one The expected product is obtained in accordance with the procedure described in Step B of Example 1, starting from 3,4-methylenedioxyaniline and the compound described in Preparation N.

Melting point: >260° C.

Elemental microanalysis:

|  | % C | % H | % N |
|---|---|---|---|
| Calculated: | 68.98 | 5.17 | 2.87 |
| Found: | 68.95 | 5.27 | 2.83 |

Elemental microanalysis: (hemihydrate)

|  | % C | % H | % N |
|---|---|---|---|
| Calculated: | 62.24 | 3.77 | 4.03 |
| Found: | 62.33 | 3.90 | 3.90 |

EXAMPLE 45

(±)-6,7-Methylenedioxy-9-(4-nitrophenyl)-4,9-dihydrofuro[3,4-b]quinolin-1(3H)-one The expected product is obtained in accordance with the procedure described in Step B of Example 1, starting from 3,4-methylenedioxyaniline and the compound described in Preparation O.

Melting point: >260° C.

Elemental microanalysis: (0.25 H$_2$O)

|  | % C | % H | % N |
|---|---|---|---|
| Calculated: | 60.59 | 3.53 | 7.85 |
| Found: | 60.86 | 3.57 | 7.62 |

EXAMPLE 46

(±)-6,7-Methylenedioxy-9-(3-nitropbenyl)-4,9-dihydrofuro[3,4-b]quinolin-1(3H)-one The expected product is obtained in accordance with the procedure described in Step B of Example 1, starting from 3,4-methylenedioxyaniline and the compound described in Preparation P.

Melting point: >260° C.

Elemental microanalysis:

|  | % C | % H | % N |
|---|---|---|---|
| Calculated: | 60.59 | 3.53 | 7.85 |
| Found: | 60.30 | 3.65 | 7.69 |

EXAMPLE 47

(±)-9-(3,5-Dimethoxy-4-hydroxyphenyl)-6,7-methylenedioxy-4,9-dihydrofuro[3,4-b]quinolin-1(3H)-one The expected product is obtained in accordance with the procedure described in Step B of Example 1, starting from 3,4-methylenedioxyaniline and the compound described in Preparation B.

Melting point: >260° C.

Elemental microanalysis: (0.25 H$_2$O)

|  | % C | % H | % N |
|---|---|---|---|
| Calculated | 61.93 | 4.55 | 3.61 |
| Found: | 61.93 | 4.59 | 3.34 |

EXAMPLE 48

(±)-9-(4-Dimethylaminophenyl)-6,7-methylenedioxy-4,9-dihydrofuro[3,4-b]quinolin-1(31)-one The expected product is obtained in accordance with the procedure described in Step B of Example 1, starting from 3,4-methylenedioxyaniline and the compound described in Preparation Q.

Melting point: >260° C.

Elemental microanalysis: (0.25 H$_2$O)

|  | % C | % H | % N |
|---|---|---|---|
| Calculated: | 67.69 | 5.25 | 7.89 |
| Found: | 67.52 | 5.29 | 7.69 |

EXAMPLE 49

(±)-6,7-Ethylenedioxy-9-(3,4,5-trimethoxyphenyl)-4,9-dihydrofuro[3,4-b]quinolin-1(3H)-one The expected product is obtained in accordance with the procedure described in Step B of Example 1, starting from 3,4-ethylenedioxyaniline and the compound described in Preparation A.

Melting point: >260° C.

Elemental microanalysis: (0.25 H$_2$O)

|  | % C | % H | % N |
|---|---|---|---|
| Calculated: | 63.53 | 5.21 | 3.37 |
| Found: | 63.56 | 5.18 | 3.39 |

EXAMPLE 50

(±)-4-Methyl-6,7-methylenedioxy-9-(4-pyridyl)-4,9-dihydrofuro[3,4-b]quinolin-1(3H)-one The expected product is obtained in accordance with the procedure described in Step B of Example 1, starting from the compound described in Step A of Example 1 and the compound described in Preparation R.

Melting point: 255° C.

Elemental microanalysis: (monohydrate)

|  | % C | % H | % N |
|---|---|---|---|
| Calculated: | 66.15 | 4.47 | 8.57 |
| Found: | 65.88 | 4.48 | 8.42 |

EXAMPLE 51

(±)-6,7-Methylenedioxy-9-(2-pyridyl)-4,9-dihydrofuro[3,4-b]quinolin-1(3H)-one

The expected product is obtained in accordance with the procedure described in Step B of Example 1, starting from 3,4-methylenedioxyaniline and the compound described in Preparation S.

Melting point: >260° C.

Elemental microanalysis:

|  | % C | % H | % N |
|---|---|---|---|
| Calculated: | 66.34 | 3.92 | 9.08 |
| Found: | 66.68 | 4.12 | 8.91 |

EXAMPLE 52

(±)-13-(3,5-Dimethoxy-4-hydroxyphenyl)-4,13-dihydronaphtho[2,3f]furo-[3,4-b]quinolin-1(3H)-one The expected product is obtained in accordance with the procedure described in Step B of Example 1, starting from 2-anthrylamine and the compound described in Preparation B.

Melting point: >260° C.

Elemental microanalysis: ($CH_3OH$)

|  | % C | % H | % N |
|---|---|---|---|
| Calculated: | 71.32 | 5.35 | 2.91 |
| Found: | 71.10 | 5.72 | 2.72 |

EXAMPLE 53

(±)-13-(3,4,5-Trimethoxyphenyl)-4,13-dihydronaphtho[2,3-f]furo-[3,4-b]quinolin-1(3H)-one The expected product is obtained in accordance with the procedure described in Step B of Example 1, starting from 2-anthrylamine and the compound described in Preparation A.

Melting point: >260° C.

Elemental microanalysis: (hemihydrate)

|  | % C | % H | % N |
|---|---|---|---|
| Calculated | 72.72 | 5.23 | 3.03 |
| Found: | 73.05 | 5.73 | 2.71 |

EXAMPLE 54

(±)-6,7-Methylenedioxy-4-(4-pyridylmethyl)-9-(3,4,5-trimethoxyphenyl)-4,9-dihydrofuro[3,4-b]quinolin-1(3H)-one The expected product is obtained in accordance with the procedure described in Example 3, starting from 3,4-methylenedioxyaniline, isonicotinaldehyde and the compound described in Preparation A.

Melting point: 240° C.

Elemental microanalysis:

|  | % C | % H | % N |
|---|---|---|---|
| Calculated: | 66.38 | 4.95 | 5.73 |
| Found: | 66.24 | 4.97 | 5.71 |

EXAMPLE 55

(±)-6,7-Methylenedioxy-4-(2-pyridylmethyl)-9-(3,4,5-trimethoxyphenyl)-4,9-dihydrofuro[3,4-b]quinolin-1(3H)-one The expected product is obtained in accordance with the procedure described in Example 3, starting from 3,4-methylenedioxyaniline, 2-pyridinecarboxaldehyde and the compound described in Preparation A.

Melting point: 258° C.

Elemental microanalysis:

|  | % C | % H | % N |
|---|---|---|---|
| Calculated: | 66.38 | 4.95 | 5.73 |
| Found: | 66.25 | 5.01 | 5.72 |

EXAMPLE 56

(±)-7-(3,4,5-Trimethoxyphenyl)-7,9,10,11-tetrahydro-8H-benzo[h]cyclopenta[b]quinolin-8-one The expected product is obtained in accordance with the procedure described in Step B of Example 1, starting from 1-naphthylamine and the compound described in Preparation L.

Melting point: 250° C.

Elemental microanalysis:

|  | % C | % H | % N |
|---|---|---|---|
| Calculated: | 74.79 | 5.77 | 3.49 |

Elemental microanalysis:

|  | % C | % H | % N |
|---|---|---|---|
| Found: | 74.46 | 6.37 | 3.09 |

EXAMPLE 57

(±)-6-Methoxy-9-(3,4,5-trimethoxyphenyl)-2,3,4,9-tetrahydro-1H-cyclopenta[b]quinolin-1-one The expected product is obtained in accordance with the procedure described in Step B of Example 1, starting from 3-methoxyaniline and the compound described in Preparation L.

Melting point: 254° C.

Elemental microanalysis: (0.25 H$_2$O)

|  | % C | % H | % N |
|---|---|---|---|
| Calculated: | 68.47 | 6.14 | 3.63 |
| Found: | 68.41 | 6.30 | 3.43 |

EXAMPLE 58

(±)-6,7-Methylenedioxy-4-(2-thienylmethyl)-9-(3,4,5-trimethoxyphenyl)-4,9-dihydrofuro[3,4-b]quinolin-1(3H)-one The expected product is obtained in accordance with the procedure described in Example 3, starting from 3,4-methylenedioxyaniline, thiophene-2-carboxaldehyde and the compound described in Preparation A.

Melting point: 230° C.

Elemental microanalysis: (0.25 H$_2$O)

|  | % C | % H | % N |
|---|---|---|---|
| Calculated: | 62.70 | 4.75 | 2.81 |
| Found: | 62.83 | 4.58 | 2.77 |

EXAMPLE 59

(±)-6,7-Methylenedioxy-4-(3-thienylmethyl)-9-(3,4,5-trimethoxyphenyl)-4,9-dihydrofuro[3,4-b]quinolin-1(3H)-one The expected product is obtained in accordance with the procedure described in Example 3, starting from 3,4-methylenedioxyaniline, thiophene-3-carboxaldehyde and the compound described in Preparation A.

Melting point: 238° C.

Elemental microanalysis:

|  | % C | % H | % N |
|---|---|---|---|
| Calculated: | 63.27 | 4.70 | 2.84 |
| Found: | 63.12 | 4.70 | 2.71 |

EXAMPLE 60

(+)-4-Methyl-6,7-methylenedioxy-9-(3,4,5-trimethoxyphenyl)-4,9-dihydrofuro[3,4-b]quinolin-1(3H)-one The expected product is obtained by separation by HPLC chromatography on a chiral column of the racemic mixture of Example 1.

EXAMPLE 61

(−)-4-Methyl-6,7-methylenedioxy-9-(3,4,5-trimethoxyphenyl)-4,9-dihydrofuro[3,4-b]quinolin-1(3H)-one The expected product is obtained by separation by HPLC chromatography on a chiral column of the racemic mixture of Example 1.

EXAMPLE 62

(±)-6-(3,4,5-Trimethoxyphenyl)-2,3,4,6,9,10-hexahydro-7H-furo[3,4-b]pyrano[3,2-g]quinolin-7-one The expected product is obtained in accordance with the procedure described in Step B of Example 1, starting from 7-chromanamine and the compound described in Preparation A.

EXAMPLE 63

(±)-9-(3,4,5-Trimethoxyphenyl)-2,3,6,9-tetrahydrofuro[3,4-b:2,3-g]quinolin-8(5H)-one The expected product is obtained in accordance with the procedure described in Step B of Example 1, starting from 2,3-dihydro-1-benzofuran-5-amine and the compound described in Preparation A.

EXAMPLE 64

(±)-9-Benzyl-6,7-methylenedioxy-4,9-dihydrofuro[3,4-b]quinolin-1(3H)-one 10 mmol of phenylacetaldehyde and 10 mmol of tetronic acid are added to 10 mmol of 3,4-methylenedioxyaniline dissolved in ethanol, then the reaction mixture is heated at reflux for the night. After returning to ambient temperature, the precipitate obtained is filtered and then washed with ethanol to yield the expected product.

EXAMPLE 65

(±)-6,7-Methylenedioxy-9-(3,4,5-trimethoxyphenyl)-3,4,9,10-tetrahydro-1(2H)-acridinone The expected product is obtained in accordance with the procedure described in Example 64, starting from 3,4- methylenedioxyaniline, 3,4,5-trimethoxybenzaldehyde and 1,3-cyclohexanedione.

EXAMPLE 66

(±)-6,7-Methylenedioxy-9-(3,4,5-trimethoxyphenyl)-4,9-dihydrothieno[3,4-b]quinolin-1(3H)-one The expected product is obtained in accordance with the procedure described in Example 64, starting from 3,4-methylenedioxyaniline, 3,4,5-trimethoxybenzaldehyde and thiotetronic acid.

Melting point: >260° C.

Elemental microanalysis:

|  | % C | % H | % N |
|---|---|---|---|
| Calculated: | 61.00 | 4.63 | 3.39 |
| Found: | 60.84 | 4.66 | 3.55 |

EXAMPLE 67

(±)-7-(3,4,5-Trimethoxyphenyl)-7,11-dihydrobenzo[h]thieno[3,4-b]quinolin-8(10H)-one The expected product is obtained in accordance with the procedure described in Example 64, starting from 1-naphthylamine, 3,4,5-trimethoxybenzaldehyde and thiotetronic acid.

Melting point: >260° C.

Elemental microanalysis:

|  | % C | % H | % N |
|---|---|---|---|
| Calculated: | 68.13 | 5.19 | 3.27 |
| Found: | 68.48 | 5.60 | 3.02 |

Pharmacological Study of the Compounds of the Invention

EXAMPLE 68

Cytotoxicity in vitro

Three cell lines are used:

1 murine leukaemia, L1210, 1 human non-small-cell lung carcinoma, A549, 1 human colon carcinoma, HT29

The cells are cultured in complete RPMI 1640 culture medium containing 10% foetal calf serum, 2 mM glutamine, 50 units/ml of penicillin, 50 µg/ml of streptomycin and 10 mM Hepes, pH=7.4. The cells are distributed in microplates and exposed to the cytotoxic compounds. The cells are then incubated for 2 days (L1210) or 4 days (A549, HT29). The number of viable cells is then quantified by means of a calorimetric assay, the Microculture Tetrazolium Assay (Cancer Res. 1987, 47, 939–942).

The results are expressed as $IC_{50}$, the concentration of cytotoxic agent that inhibits the proliferation of the treated cells by 50%. By way of example, the compounds of Examples 1, 8 and 10 have the $IC_{50}$s set out in the Table below:

| | $IC_{50}$ nM | | |
|---|---|---|---|
| Compounds tested | L1210 | A549 | HT29 |
| Example 1 | 53 | 102 | 104 |
| Example 8 | 62 | 147 | 153 |
| Example 10 | 12 | 22 | 18 |

EXAMPLE 69

In vivo Activity: Anti-tumour Activity of the Compounds on P388 Leukaemia

Line P388 (murine leukaemia) was supplied by the National Cancer Institute (Frederick, USA). The tumour cells (106 cells) were inoculated on day 0 into the peritoneal cavity of female BDF1 mice (Iffa-Credo, France) weighing from 18 to 20 g (groups of 6 animals). The products were administered by the intraperitoneal route on day 1 (D1).

The anti-tumour activity is expressed as % T/C:

$$\% \ T/C = \frac{\text{Median survival time of the treated animals}}{\text{Median survival time of the control animals}} \times 100$$

By way of example, the compound of Example 1 is active from the 50 mg/kg dose and enables the survival of the treated animals to be doubled (T/C≧200%).

EXAMPLE 70

Pharmaceutical Composition

Formulation for the preparation of 1000 tablets each comprising 10 mg of active ingredient compound of Example 1 . . . 10 g hydroxypropyl cellulose . . . 2 g wheat starch . . . 10 g lactose . . . 100 g magnesium stearate . . . 3 g talc . . . 3 g

We claim:

1. A compound selected from those of formula (I):

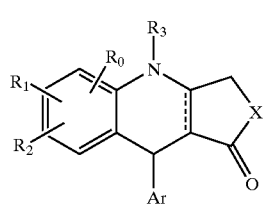

(I)

wherein:

=== represents a single or double bond, $R_0$ represents hydrogen, hydroxy or linear or branched ($C_1$–$C_6$)alkoxy, $R_1$ and $R_2$, which are identical or different, each represents:

hydrogen, linear or branched ($C_1$–$C_6$)alkyl, linear or branched ($C_1$–$C_6$)alkoxy, hydroxy, linear or branched ($C_1$–$C_6$)polyhaloalkyl, nitro,
amino optionally substituted by one or two linear or branched $(C_1-C_6)$alkyl groups,
a group of formula

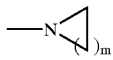

wherein m is 1 to 4 inclusive, or form together with the carbon atoms carrying them an aromatic or non-aromatic, mono-or bi-cyclic group having from 5 to 12 ring members, optionally containing 1 or 2 hetero atoms selected from O, S and N, $R_3$ represents hydrogen or a group of formula $R_4$ wherein $R_4$ represents:
aryl,
heteroaryl,
$(C_3-C_8)$cycloalkyl,
linear or branched $(C_1-C_6)$alkyl optionally substituted by aryl, by heteroaryl, by hydroxy, by linear or branched $(C_1-C_6)$alkoxy, or by a group of formula $NR_5R_6$ wherein $R_5$ and $R_6$, which are identical or different, each represents linear or branched $(C_1-C_6)$alkyl or linear or branched $(C_1-C_6)$hydroxyalkyl, or form together with the nitrogen atom carrying them a nitrogen heterocycle,
or a group of formula $COR_7$, wherein $R_7$ represents one of the following groups:
aryl,
linear or branched $(C_1-C_6)$alkyl (optionally substituted by a group of formula $NR_8R_9$ wherein $R_8$ and $R_9$, which are identical or different, each represents linear or branched $(C_1-C_6)$alkyl or linear or branched $(C_1-C_6)$hydroxyalkyl, or form together with the nitrogen atom carrying them a nitrogen heterocycle),
amino optionally substituted by one or more groups aryl, heteroaryl, or linear or branched $(C_1-C_6)$ alkyl optionally substituted by a group of formula $NR_8R_9$ wherein $R_8$ and $R_9$, which are identical or different, each represents linear or branched $(C_1-C_6)$alkyl or linear or branched $(C_1-C_6)$ hydroxyalkyl, or form together with the nitrogen atom carrying them a nitrogen heterocycle,
or $OR_{10}$ wherein $R_{10}$ represents hydrogen or aryl, or linear or branched $(C_1-C_6)$alkyl optionally substituted by a group of formula $NR_8R_9$ wherein $R_8$ and $R_9$, which are identical or different, each represents linear or branched $(C_1-C_6)$alkyl or linear or branched $(C_1-C_6)$hydroxyalkyl, or form together with the nitrogen atom carrying them a nitrogen heterocycle,
X represents oxygen or sulphur or $-CH_2-$ or $-CH_2-CH_2-$,
Ar represents aryl, heteroaryl or aryl-$(C_1-C_6)$alkyl in which alkyl is linear or branched, it being understood that a least one of $R_0$, $R_1$, or $R_2$ is other than hydrogen,
their optical isomers, their hydrates, solvates and also addition salts thereof with a pharmaceutically acceptable acid, wherein aryl is to be understood as phenyl, biphenyl, naphthyl or tetrahydronaphthyl, each of those groups being optionally substituted by one or more identical or different atoms or groups selected from halogen and linear or branched $(C_1-C_6)$alkyl, hydroxy, linear or branched $(C_1-C_6)$ alkoxy, linear or branched $(C_1-C_6)$polyhaloalkyl, amino (optionally substituted by one or more linear or branched $(C_1-C_6)$alkyl groups), nitro, linear or branched $(C_1-C_6)$acyl and $(C_1-C_2)$alkylenedioxy, heteroaryl is to be understood as an aromatic, mono- or bi-cyclic group having from 5 to 12 ring members and containing one, two or three hetero atoms selected from oxygen, nitrogen and sulphur, wherein the heteroaryl group may be optionally substituted by one or more identical or different atoms or groups selected from halogen and linear or branched $(C_1-C_6)$alkyl, hydroxy, linear or branched $(C_1-C_6)$alkoxy, linear or branched $(C_1-C_6)$polyhaloalkyl, and amino (optionally substituted by one or more linear or branched $(C_1-C_6)$alkyl groups), and a nitrogen heterocycle is to be understood as a saturated monocyclic group having from 5 to 7 ring members and containing one, two or three hetero atoms, one of which is nitrogen while the additional hetero atoms(s) optionally present is/are selected from oxygen, nitrogen and sulphur.

2. A compound of claim 1, wherein === represents a double bond.

3. A compound of claim 1, wherein $R_0$ represents hydrogen.

4. A compound of claim 1, wherein $R_1$ and $R_2$, which are identical or different, each represents:
hydrogen,
linear or branched $(C_1-C_6)$alkyl,
linear or branched $(C_1-C_6)$alkoxy,
hydroxy,
linear or branched $(C_1-C_6)$polyhaloalkyl,
nitro,
amino optionally substituted by one or two linear or branched $(C_1-C_6)$alkyl groups,
a group of formula

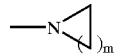

wherein m is 1 to 4 inclusive.

5. A compound of claim 1, wherein $R_1$ and $R_2$ form together with the carbon atoms carrying them an aromatic or non-aromatic, mono- or bi-cyclic group having from 5 to 12 ring members and optionally containing 1 or 2 hetero atoms selected from O, S and N.

6. A compound of claim 5, wherein $R_1$ and $R_2$ form together with the carbon atoms carrying them a group of formula $G_3$ or $G_4$:

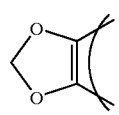

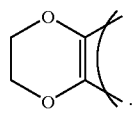

7. A compound of claim 5, wherein $R_1$ and $R_2$ form together with the carbon atoms carrying them phenylene.

8. A compound of claim 1, wherein X represents oxygen.

9. A compound of claims 1, wherein X represents sulphur.

10. A compound of claim 1, wherein X represents $-CH_2-$ or $-CH_2-CH_2-$.

11. A compound of claim 1, wherein Ar represents aryl.

12. A compound of claim 1, wherein Ar represents heteroaryl.

13. A compound of claim 11, wherein Ar represents phenyl.

14. A compound of claim 1 selected from (±)-4-methyl-6,7-methylenedioxy-9-(3,4,5-trimethoxyphenyl)-4,9-dihydrofuro[3,4-b]quinolin-1(3H)-one, and also its optical isomers and its hydrates and solvates.

15. A compound of claim 1 selected from (±)-6,7-methylenedioxy-9-(3,4,5-trimethoxyphenyl)-4,9-dihydrofuro[3,4-b]quinolin-1(3H)-one, its optical isomers, its hydrates, solvates, and also its addition salts with a pharmaceutically acceptable acid.

16. A compound of claim 1 selected from (±)-6-methoxy-9-(3,4,5-trimethoxyphenyl)-4,9-dihydrofuro[3,4-b]quinolin-1(3H)-one, its optical isomers, its hydrates, solvates, and also its addition salts with a pharmaceutically acceptable acid.

17. A compound of claim 1 selected from (±)-7-(3,4,5-trimethoxyphenyl)-7,11-dihydrobenzo[h]furo[3,4-b]quinolin-8(10H)-one, its optical isomers, its hydrates, solvates, and also its addition salts with a pharmaceutically acceptable acid.

18. A compound of claim 1 selected from (±)-6,7-methylenedioxy-9-(3,4,5-trimethoxyphenyl)-2,3,4,9-tetrahydrocyclopenta[b]quinolin-1-one, its optical isomers, its hydrates, solvates, and also its addition salts with a pharmaceutically acceptable acid.

19. A compound of claim 1 selected from (±)-6,7-ethylenedioxy-9-(3,4,5-trimethoxyphenyl)-4,9-dihydrofuro[3,4-b]quinolin-1(3H)-one, its optical isomers, its hydrates, solvates, and also its addition salts with a pharmaceutically acceptable acid.

20. A compound of claim 1 selected from (±)-7-(3,4,5-trimethoxyphenyl)-7,9,10,11-tetrahydro-8H-benzo[h]cyclopenta[b]quinolin-8-one, its optical isomers, its hydrates, solvates, and also its addition salts with a pharmaceutically acceptable acid.

21. A method for treating a living body afflicted with a cancer selected from leukemia, lung carcinoma, and colon carcinoma, comprising the step of administering to the living body in need thereof an amount of a compound of claim 1 which is effective for alleviation of said cancer.

22. A pharmaceutical composition comprising, a compound as claimed in claim 1, together with one or more pharmaceutically acceptable excipients or vehicles.

* * * * *

UNITED STATES PATENT AND TRADEMARK OFFICE
CERTIFICATE OF CORRECTION

PATENT NO. : 6,548,515 B1
DATED : April 15, 2003
INVENTOR(S) : Henri-Philippe Husson et al.

It is certified that error appears in the above-identified patent and that said Letters Patent is hereby corrected as shown below:

<u>Title page,</u>
Item [73], Assignee, "Les Laboratories Servier" should be -- Les Laboratoires Servier --.
Item [*] Notice, "156 days" should be -- 158 days --.

Signed and Sealed this

Tenth Day of February, 2004

JON W. DUDAS
*Acting Director of the United States Patent and Trademark Office*